US012781226B2

(12) United States Patent
Thompson

(10) Patent No.: US 12,781,226 B2
(45) Date of Patent: Nov. 3, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/195,132

(22) Filed: Apr. 30, 2025

(65) Prior Publication Data

US 2026/0103711 A1 Apr. 16, 2026

Related U.S. Application Data

(63) Continuation of application No. 18/913,381, filed on Oct. 11, 2024.

(51) Int. Cl.
*C12N 15/113* (2010.01)
*C12N 15/86* (2006.01)

(52) U.S. Cl.
CPC .......... *C12N 15/1136* (2013.01); *C12N 15/86* (2013.01); *C12N 2310/141* (2013.01); *C12N 2750/14143* (2013.01)

(58) Field of Classification Search
CPC .............. A61K 31/7088; C12N 15/113; C12N 2310/141
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Minshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 | 11/2024 | Thompson | |
| 2012/0064122 A1* | 3/2012 | Baltimore | A61P 17/06 435/375 |
| 2024/0026377 A1 | 1/2024 | Thompson | |

FOREIGN PATENT DOCUMENTS

| | | | |
|---|---|---|---|
| CA | 2721333 A1 | 10/2009 | |
| WO | 2011032100 A1 | 3/2011 | |

OTHER PUBLICATIONS

Brain et al., The intracellular sensor NOD2 induces microRNA-29 expression in human dendritic cells to limit IL-23 release, Immunity, vol. 39, pp. 521-536. (Year: 2013).*
Salvi et al. "Cytokine targeting by miRNAs in autoimmune diseases." Frontiers in immunology 10 (2019): 15.
Bao et al. "miRNA-21 promotes the progression of acute liver failure via the KLF6/autophagy/IL-23 signaling pathway." Molecular Medicine Reports 29.5 (2024): 80.
Bottoni et al. "Targeting BTK through microRNA in chronic lymphocytic leukemia." Blood, The Journal of the American Society of Hematology 128.26 (2016): 3101-3112.
Brutons Tyrosine Kinase Genbank Sequence (2023).
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Nature (2010. Gene Expression. Scitable. Available online at Nature.com) <https://www.nature.com/scitable/topicpage/gene-expression-14121669> (2010).
GenBank EGF Sequence (2023).
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI Nucleotide Sequence ALK Lingand, search performed Dec. 26, 2024 (2023).
NCBI Nucleotide Sequence ALK Receptor, search performed Dec. 26, 2024 (2023).
GenBank EGFR Sequence (2023).
Genbank FLT3 Sequence (2024).
NCBI Nucleotide Sequence for PARP, search performed Dec. 26, 2024 (2024).
Tritschler et al. "Concepts and limitations for learning developmental trajectories from single cell genomics." Development 146.12 (2019): dev170506.
Kondratov et al. "Direct head-to-head evaluation of recombinant adeno-associated viral vectors manufactured in human versus insect cells." Molecular Therapy 25.12 (2017): 2661-2675.
O'Brien et al. Overview of MicroRNA Biogenesis, Mechanisms of Actions, and Circulation, Frontiers in Endocrinology, vol. 9, Article 402: 1-12 (2018). (Year: 2018).
Gorski, S., Vogel, J. & Doudna, J. RNA-based recognition and targeting: sowing the seeds of specificity. Nat Rev Mol Cell Biol 18, 215-228 (2017). (Year: 2017).

(Continued)

*Primary Examiner* — Ram R Shukla
*Assistant Examiner* — Shabana S Meyering
(74) *Attorney, Agent, or Firm* — Gowling WLG (Canada) LLP

(57) ABSTRACT

The embodiments of the present disclosure relate to decreasing the bioavailability of one or more target biomolecules by providing a composition that comprises a recombinant plasmid (RP) and one or more sequences of micro-interfering ribonucleic acid (miRNA). When the RP interacts with a target cell, it causes the target cell to upregulate production of the miRNA, which then decreases the bioavailability of the target biomolecule. In some embodiments of the present disclosure, the target biomolecule is a cytokine or other mediator molecule of an inflammatory response.

2 Claims, No Drawings

Specification includes a Sequence Listing.

(56) References Cited

OTHER PUBLICATIONS

Denzler R et al. Impact of MicroRNA Levels, Target-Site Complementarity, and Cooperativity on Competing Endogenous RNA-Regulated Gene Expression. Mol Cell. Nov. 3, 2016;64(3):565-579. doi: 10.1016/j.molcel.2016.09.027 (Year: 2016).

Wang et al. “Adeno-associated virus vector as a platform for gene therapy delivery”. Nat Rev Drug Discov. May 2019;18(5):358-378. (Year: 2019).

Van den Berg, et al. “Design of Effective Primary MicroRNA Mimics with Different Basal Stem Conformations.” Molecular Therapy—Nucleic Acids, vol. 5, 2016, e278, pp. 1-12 (Year: 2016).

* cited by examiner

SEQUENCE LISTING

```
Sequence total quantity: 3
SEQ ID NO: 1            moltype = DNA  length = 5807
FEATURE                 Location/Qualifiers
source                  1..5807
                        mol_type = other DNA
                        organism = synthetic construct
SEQUENCE: 1
tctagaataa tcaacctctg gattacaaaa tttgtgaaag attgactggt attcttaact  60
atgttgctcc ttttacgcta tgtggatacg ctgctttaat gcctttgtat catgctattg  120
cttcccgtat ggctttcatt ttctcctcct tgtataaatc ctggttgctg tctctttatg  180
aggagttgtg gcccgttgtc aggcaacgtg gcgtggtgtg cactgtgttt gctgacgcaa  240
cccccactgg ttggggcatt gccaccacct gtcagctcct ttccgggact ttcgctttcc  300
ccctccctat tgccacggcg gaactcatcg ccgcctgcct tgcccgctgc tggacagggg  360
ctcggctgtt gggcactgac aattccgtgg tgttgtcggg gaaatcatcg tcctttcctt  420
ggctgctcgc ctgtgttgcc acctggattc tgcgcgggac gtccttctgc tacgtccctt  480
cggccctcaa tccagcggac cttccttccc gcggcctgct gccggctctg cggcctcttc  540
cgcgtcttcg ccttcgccct cagacgagtc ggatctccct ttgggccgcc tccccgccta  600
agcttatcga taccgtcgag atctaacttg tttattgcag cttataatgg ttacaaataa  660
agcaatagca tcacaaattt cacaaataaa gcattttttt cactgcattc tagttgtggt  720
ttgtccaaac tcatcaatgt atcttatcat gtctggatct cgacctcgac tagagcatgg  780
ctacgtagat aagtagcatg gcgggttaat cattaactac aaggaacccc tagtgatgga  840
gttggccact ccctctctgc gcgctcgctc gctcactgag gccgggcgac caaaggtcgc  900
```

```
ccgacgcccg ggctttgccc gggcggcctc agtgagcgag cgagcgcgca gctggcgtaa  960
tagcgaagag gcccgcaccg atcgcccttc ccaacagttg cgcagcctga atggcgaatg  1020
gcgattccgt tgcaatggct ggcggtaata ttgttctgga tattaccagc aaggccgata  1080
gtttgagttc ttctactcag gcaagtgatg ttattactaa tcaaagaagt attgcgacaa  1140
cggttaattt gcgtgatgga cagactcttt tactcggtgg cctcactgat tataaaaaca  1200
cttctcagga ttctggcgta ccgttcctgt ctaaaatccc tttaatcggc ctcctgttta  1260
gctcccgctc tgattctaac gaggaaagca cgttatacgt gctcgtcaaa gcaaccatag  1320
tacgcgccct gtagcggcgc attaagcgcg gcgggtgtgg tggttacgcg cagcgtgacc  1380
gctacacttg ccagcgccct agcgcccgct cctttcgctt tcttcccttc ctttctcgcc  1440
acgttcgccg gctttccccg tcaagctcta aatcgggggc tccctttagg gttccgattt  1500
agtgctttac ggcacctcga ccccaaaaaa cttgattagg gtgatggttc acgtagtggg  1560
ccatcgccct gatagacggt ttttcgccct ttgacgttgg agtccacgtt ctttaatagt  1620
ggactcttgt tccaaactgg aacaacactc aaccctatct cggtctattc ttttgattta  1680
taagggattt tgccgatttc ggcctattgg ttaaaaaatg agctgattta acaaaaattt  1740
aacgcgaatt ttaacaaaat attaacgttt acaatttaaa tatttgctta tacaatcttc  1800
ctgtttttgg ggcttttctg attatcaacc ggggtacata tgattgacat gctagtttta  1860
cgattaccgt tcatcgattc tcttgtttgc tccagactct caggcaatga cctgatagcc  1920
tttgtagaga cctctcaaaa atagctaccc tctccggcat gaatttatca gctagaacgg  1980
ttgaatatca tattgatggt gatttgactg tctccggcct ttctcacccg tttgaatctt  2040
tacctacaca ttactcaggc attgcattta aaatatatga gggttctaaa aatttttatc  2100
cttgcgttga aataaaggct tctcccgcaa aagtattaca gggtcataat gtttttggta  2160
caaccgattt agctttatgc tctgaggctt tattgcttaa ttttgctaat tctttgcctt  2220
gcctgtatga tttattggat gttggaattc ctgatgcggt attttctcct tacgcatctg  2280
tgcggtattt cacaccgcat atggtgcact ctcagtacaa tctgctctga tgccgcatag  2340
ttaagccagc cccgacaccc gccaacaccc gctgacgcgc cctgacgggc ttgtctgctc  2400
ccggcatccg cttacagaca agctgtgacc gtctccggga gctgcatgtg tcagaggttt  2460
tcaccgtcat caccgaaacg cgcgagacga aagggcctcg tgatacgcct atttttatag  2520
gttaatgtca tgataataat ggtttcttag acgtcaggtg gcacttttcg gggaaatgtg  2580
cgcggaaccc ctatttgttt atttttctaa atacattcaa atatgtatcc gctcatgaga  2640
caataaccct gataaatgct tcaataatat tgaaaaagga agagtatgag tattcaacat  2700
ttccgtgtcg cccttattcc cttttttgcg gcattttgcc ttcctgtttt tgctcaccca  2760
gaaacgctgg tgaaagtaaa agatgctgaa gatcagttgg gtgcacgagt gggttacatc  2820
gaactggatc tcaacagcgg taagatcctt gagagttttc gccccgaaga acgttttcca  2880
atgatgagca cttttaaagt tctgctatgt ggcgcggtat tatcccgtat tgacgccggg  2940
caagagcaac tcggtcgccg catacactat tctcagaatg acttggttga gtactcacca  3000
gtcacagaaa agcatcttac ggatggcatg acagtaagag aattatgcag tgctgccata  3060
accatgagtg ataacactgc ggccaactta cttctgacaa cgatcggagg accgaaggag  3120
ctaaccgctt ttttgcacaa catgggggat catgtaactc gccttgatcg ttgggaaccg  3180
gagctgaatg aagccatacc aaacgacgag cgtgacacca cgatgcctgt agcaatggca  3240
acaacgttgc gcaaactatt aactggcgaa ctacttactc tagcttcccg gcaacaatta  3300
atagactgga tggaggcgga taaagttgca ggaccacttc tgcgctcggc ccttccggct  3360
ggctggttta ttgctgataa atctggagcc ggtgagcgtg ggtctcgcgg tatcattgca  3420
gcactggggc cagatggtaa gccctcccgt atcgtagtta tctacacgac ggggagtcag  3480
gcaactatgg atgaacgaaa tagacagatc gctgagatag gtgcctcact gattaagcat  3540
tggtaactgt cagaccaagt ttactcatat atactttaga ttgatttaaa acttcatttt  3600
taatttaaaa ggatctaggt gaagatcctt tttgataatc tcatgaccaa aatcccttaa  3660
cgtgagtttt cgttccactg agcgtcagac cccgtagaaa agatcaaagg atcttcttga  3720
gatccttttt ttctgcgcgt aatctgctgc ttgcaaacaa aaaaaccacc gctaccagcg  3780
gtggtttgtt tgccggatca agagctacca actctttttc cgaaggtaac tggcttcagc  3840
agagcgcaga taccaaatac tgtccttcta gtgtagccgt agttaggcca ccacttcaag  3900
aactctgtag caccgcctac atacctcgct ctgctaatcc tgttaccagt ggctgctgcc  3960
agtggcgata agtcgtgtct taccgggttg gactcaagac gatagttacc ggataaggcg  4020
cagcggtcgg gctgaacggg gggttcgtgc acacagccca gcttggagcg aacgacctac  4080
accgaactga gatacctaca gcgtgagcta tgagaaagcg ccacgcttcc cgaagggaga  4140
aaggcggaca ggtatccggt aagcggcagg gtcggaacag gagagcgcac gagggagctt  4200
ccagggggaa acgcctggta tctttatagt cctgtcgggt ttcgccacct ctgacttgag  4260
cgtcgatttt tgtgatgctc gtcagggggg cggagcctat ggaaaaacgc cagcaacgcg  4320
gcctttttac ggttcctggc cttttgctgg ccttttgctc acatgttctt tcctgcgtta  4380
tcccctgatt ctgtggataa ccgtattacc gcctttgagt gagctgatac cgctcgccgc  4440
agccgaacga ccgagcgcag cgagtcagtg agcgaggaag cggaagagcg cccaatacgc  4500
aaaccgcctc tccccgcgcg ttggccgatt cattaatgca gcagctgcgc gctcgctcgc  4560
tcactgaggc cgcccgggca aagcccgggc gtcgggcgac ctttggtcgc ccggcctcag  4620
tgagcgagcg agcgcgcaga gagggagtgg ccaactccat cactaggggt tccttgtagt  4680
taatgattaa cccgccatgc tacttatcta cgtagccatg ctctaggaca ttgattattg  4740
actagtggag ttccgcgtta cataacttac ggtaaatggc ccgcctggct gaccgcccaa  4800
cgacccccgc ccattgacgt caataatgac gtatgttccc atagtaacgc caatagggac  4860
tttccattga cgtcaatggg tggagtattt acggtaaact gcccacttgg cagtacatca  4920
agtgtatcat atgccaagta cgccccctat tgacgtcaat gacggtaaat ggcccgcctg  4980
gcattatgcc cagtacatga ccttatggga ctttcctact tggcagtaca tctacgtatt  5040
agtcatcgct attaccatgg tcgaggtgag ccccacgttc tgcttcactc tccccatctc  5100
ccccccctcc ccacccccaa ttttgtattt atttattttt taattatttt gtgcagcgat  5160
gggggcgggg gggggggggg gcgcgcgcca ggcggggcgg ggcggggcga ggggcggggc  5220
ggggcgaggc ggagaggtgc ggcggcagcc aatcagagcg gcgcgctccg aaagtttcct  5280
tttatggcga ggcggcggcg gcggcggccc tataaaaagc gaagcgcgcg gcgggcggga  5340
gtcgctgcgc gctgccttcg ccccgtgccc cgctccgccg ccgcctcgcg ccgcccgccc  5400
cggctctgac tgaccgcgtt actaaaacag gtaagtccgg cctccgcgcc gggttttggc  5460
gcctcccgcg ggcgcccccc tcctcacggc gagcgctgcc acgtcagacg aagggcgcag  5520
cgagcgtcct gatccttccg cccggacgct caggacagcg gcccgctgct cataagactc  5580
ggccttagaa ccccagtatc agcagaagga catttagga cgggacttgg gtgactctag  5640
```

-continued

```
ggcactggtt ttctttccag agagcggaac aggcgaggaa aagtagtccc ttctcggcga  5700
ttctgcggag ggatctccgt ggggcggtga acgccgatga tgcctctact aaccatgttc  5760
atgttttctt ttttttcta caggtcctgg gtgacgaaca gggtacc                5807

SEQ ID NO: 2            moltype = DNA  length = 524
FEATURE                 Location/Qualifiers
source                  1..524
                        mol_type = other DNA
                        organism = synthetic construct
SEQUENCE: 2
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgtt tcttcatcgt gccttcttcg cgttttggcc tctgactgac  180
gcgaagaagg cgatgaagaa acaggacaca aggcctgtta ctagcactca catggaacaa  240
atggcctcta gcctggaggc ttgctgaagg ctgtatgctg tcttcatcgc catttcttcg  300
cgttttggcc tctgactgac gcgaagaagg cgatgaagac aggacacaag gcctgttact  360
agcactcaca tggaacaaat ggcctctagc ctggaggctt gctgaaggct gtatgctgaa  420
actggctgta atatcgcgcg ttttggcctc tgactgacgc gcgataacag ccagtttcag  480
gacacaaggc ctgttactag cactcacatg gaacaaatgg cctc                   524

SEQ ID NO: 3            moltype = DNA  length = 6331
FEATURE                 Location/Qualifiers
source                  1..6331
                        mol_type = other DNA
                        organism = synthetic construct
SEQUENCE: 3
tctagaataa tcaacctctg gattacaaaa tttgtgaaag attgactggt attcttaact  60
atgttgctcc ttttacgcta tgtggatacg ctgctttaat gcctttgtat catgctattg  120
cttcccgtat ggctttcatt ttctcctcct tgtataaatc ctggttgctg tctctttatg  180
aggagttgtg gcccgttgtc aggcaacgtg gcgtggtgtg cactgtgttt gctgacgcaa  240
cccccactgg ttggggcatt gccaccacct gtcagctcct ttccgggact ttcgctttcc  300
ccctccctat tgccacggcg gaactcatcg ccgcctgcct tgcccgctgc tggacagggg  360
ctcggctgtt gggcactgac aattccgtgg tgttgtcggg gaaatcatcg tcctttcctt  420
ggctgctcgc ctgtgttgcc acctggattc tgcgcgggac gtccttctgc tacgtccctt  480
cggccctcaa tccagcggac cttccttccc gcggcctgct gccggctctg cggcctcttc  540
cgcgtcttcg ccttcgccct cagacgagtc ggatctccct ttgggccgcc tccccgccta  600
agcttatcga taccgtcgag atctaacttg tttattgcag cttataatgg ttacaaataa  660
agcaatagca tcacaaattt cacaaataaa gcattttttt cactgcattc tagttgtggt  720
ttgtccaaac tcatcaatgt atcttatcat gtctggatct cgacctcgac tagagcatgg  780
ctacgtagat aagtagcatg gcgggttaat cattaactac aaggaacccc tagtgatgga  840
gttggccact ccctctctgc gcgctcgctc gctcactgag gccgggcgac caaaggtcgc  900
ccgacgcccg ggctttgccc gggcggcctc agtgagcgag cgagcgcgca gctggcgtaa  960
tagcgaagag gcccgcaccg atcgcccttc ccaacagttg cgcagcctga atggcgaatg  1020
gcgattccgt tgcaatggct ggcggtaata ttgttctgga tattaccagc aaggccgata  1080
gtttgagttc ttctactcag gcaagtgatg ttattactaa tcaaagaagt attgcgacaa  1140
cggttaattt gcgtgatgga cagactcttt tactcggtgg cctcactgat tataaaaaca  1200
cttctcagga ttctggcgta ccgttcctgt ctaaaatccc tttaatcggc ctcctgttta  1260
gctcccgctc tgattctaac gaggaaagca cgttatacgt gctcgtcaaa gcaaccatag  1320
tacgcgccct gtagcggcgc attaagcgcg gcgggtgtgg tggttacgcg cagcgtgacc  1380
gctacacttg ccagcgccct agcgcccgct cctttcgctt tcttcccttc ctttctcgcc  1440
acgttcgccg gctttccccg tcaagctcta aatcgggggc tccctttagg gttccgattt  1500
agtgctttac ggcacctcga ccccaaaaaa cttgattagg gtgatggttc acgtagtggg  1560
ccatcgccct gatagacggt ttttcgccct ttgacgttgg agtccacgtt ctttaatagt  1620
ggactcttgt tccaaactgg aacaacactc aaccctatct cggtctattc ttttgattta  1680
taagggattt tgccgatttc ggcctattgg ttaaaaaatg agctgattta acaaaaattt  1740
aacgcgaatt ttaacaaaat attaacgttt acaatttaaa tatttgctta tacaatcttc  1800
ctgtttttgg ggcttttctg attatcaacc ggggtacata tgattgacat gctagtttta  1860
cgattaccgt tcatcgattc tcttgtttgc tccagactct caggcaatga cctgatagcc  1920
tttgtagaga cctctcaaaa atagctaccc tctccggcat gaatttatca gctagaacgg  1980
ttgaatatca tattgatggt gatttgactg tctccggcct ttctcacccg tttgaatctt  2040
tacctacaca ttactcaggc attgcattta aaatatatga gggttctaaa aatttttatc  2100
cttgcgttga aataaaggct tctcccgcaa aagtattaca gggtcataat gtttttggta  2160
caaccgattt agctttatgc tctgaggctt tattgcttaa ttttgctaat tctttgcctt  2220
gcctgtatga tttattggat gttggaattc ctgatgcggt attttctcct tacgcatctg  2280
tgcggtattt cacaccgcat atggtgcact ctcagtacaa tctgctctga tgccgcatag  2340
ttaagccagc cccgacaccc gccaacaccc gctgacgcgc cctgacgggc ttgtctgctc  2400
ccggcatccg cttacagaca agctgtgacc gtctccggga gctgcatgtg tcagaggttt  2460
tcaccgtcat caccgaaacg cgcgagacga aagggcctcg tgatacgcct atttttatag  2520
gttaatgtca tgataataat ggtttcttag acgtcaggtg gcacttttcg gggaaatgtg  2580
cgcggaaccc ctatttgttt atttttctaa atacattcaa atatgtatcc gctcatgaga  2640
caataaccct gataaatgct tcaataatat tgaaaaagga agagtatgag tattcaacat  2700
ttccgtgtcg cccttattcc cttttttgcg gcattttgcc ttcctgtttt tgctcaccca  2760
gaaacgctgg tgaaagtaaa agatgctgaa gatcagttgg gtgcacgagt gggttacatc  2820
gaactggatc tcaacagcgg taagatcctt gagagttttc gccccgaaga acgttttcca  2880
atgatgagca cttttaaagt tctgctatgt ggcgcggtat tatcccgtat tgacgccggg  2940
caagagcaac tcggtcgccg catacactat tctcagaatg acttggttga gtactcacca  3000
gtcacagaaa agcatcttac ggatggcatg acagtaagag aattatgcag tgctgccata  3060
accatgagtg ataacactgc ggccaactta cttctgacaa cgatcggagg accgaaggag  3120
ctaaccgctt ttttgcacaa catgggggat catgtaactc gccttgatcg ttgggaaccg  3180
```

-continued

```
gagctgaatg aagccatacc aaacgacgag cgtgacacca cgatgcctgt agcaatggca  3240
acaacgttgc gcaaactatt aactggcgaa ctacttactc tagcttcccg gcaacaatta  3300
atagactgga tggaggcgga taaagttgca ggaccacttc tgcgctcggc ccttccggct  3360
ggctggttta ttgctgataa atctggagcc ggtgagcgtg ggtctcgcgg tatcattgca  3420
gcactggggc cagatggtaa gccctcccgt atcgtagtta tctacacgac ggggagtcag  3480
gcaactatgg atgaacgaaa tagacagatc gctgagatag gtgcctcact gattaagcat  3540
tggtaactgt cagaccaagt ttactcatat atactttaga ttgatttaaa acttcatttt  3600
taatttaaaa ggatctaggt gaagatcctt tttgataatc tcatgaccaa aatcccttaa  3660
cgtgagtttt cgttccactg agcgtcagac cccgtagaaa agatcaaagg atcttcttga  3720
gatccttttt ttctgcgcgt aatctgctgc ttgcaaacaa aaaaaccacc gctaccagcg  3780
gtggtttgtt tgccggatca agagctacca actctttttc cgaaggtaac tggcttcagc  3840
agagcgcaga taccaaatac tgtccttcta gtgtagccgt agttaggcca ccacttcaag  3900
aactctgtag caccgcctac atacctcgct ctgctaatcc tgttaccagt ggctgctgcc  3960
agtggcgata agtcgtgtct taccgggttg gactcaagac gatagttacc ggataaggcg  4020
cagcggtcgg gctgaacggg gggttcgtgc acacagccca gcttggagcg aacgacctac  4080
accgaactga gatacctaca gcgtgagcta tgagaaagcg ccacgcttcc cgaagggaga  4140
aaggcggaca ggtatccggt aagcggcagg gtcggaacag gagagcgcac gagggagctt  4200
ccagggggaa acgcctggta tctttatagt cctgtcgggt ttcgccacct ctgacttgag  4260
cgtcgatttt tgtgatgctc gtcagggggg cggagcctat ggaaaaacgc cagcaacgcg  4320
gcctttttac ggttcctggc cttttgctgg ccttttgctc acatgttctt tcctgcgtta  4380
tcccctgatt ctgtggataa ccgtattacc gcctttgagt gagctgatac cgctcgccgc  4440
agccgaacga ccgagcgcag cgagtcagtg agcgaggaag cggaagagcg cccaatacgc  4500
aaaccgcctc tccccgcgcg ttggccgatt cattaatgca gcagctgcgc gctcgctcgc  4560
tcactgaggc cgcccgggca aagcccgggc gtcgggcgac ctttggtcgc ccggcctcag  4620
tgagcgagcg agcgcgcaga gagggagtgg ccaactccat cactaggggt tccttgtagt  4680
taatgattaa cccgccatgc tacttatcta cgtagccatg ctctaggaca ttgattattg  4740
actagtggag ttccgcgtta cataacttac ggtaaatggc ccgcctggct gaccgcccaa  4800
cgacccccgc ccattgacgt caataatgac gtatgttccc atagtaacgc caatagggac  4860
tttccattga cgtcaatggg tggagtattt acggtaaact gcccacttgg cagtacatca  4920
agtgtatcat atgccaagta cgccccctat tgacgtcaat gacggtaaat ggcccgcctg  4980
gcattatgcc cagtacatga ccttatggga ctttcctact tggcagtaca tctacgtatt  5040
agtcatcgct attaccatgg tcgaggtgag ccccacgttc tgcttcactc tccccatctc  5100
ccccccctcc ccacccccaa ttttgtattt atttattttt taattatttt gtgcagcgat  5160
gggggcgggg gggggggggg gcgcgcgcca ggcggggcgg ggcggggcga ggggcggggc  5220
ggggcgaggc ggagaggtgc ggcggcagcc aatcagagcg gcgcgctccg aaagtttcct  5280
tttatggcga ggcggcggcg gcggcggccc tataaaaagc gaagcgcgcg gcgggcggga  5340
gtcgctgcgc gctgccttcg ccccgtgccc cgctccgccg ccgcctcgcg ccgcccgccc  5400
cggctctgac tgaccgcgtt actaaaacag gtaagtccgg cctccgcgcc gggttttggc  5460
gcctcccgcg ggcgcccccc tcctcacggc gagcgctgcc acgtcagacg aagggcgcag  5520
cgagcgtcct gatccttccg cccggacgct caggacagcg gcccgctgct cataagactc  5580
ggccttagaa ccccagtatc agcagaagga cattttagga cgggacttgg gtgactctag  5640
ggcactggtt ttctttccag agagcggaac aggcgaggaa aagtagtccc ttctcggcga  5700
ttctgcggag ggatctccgt ggggcggtga acgccgatga tgcctctact aaccatgttc  5760
atgttttctt ttttttttcta caggtcctgg gtgacgaaca gggtaccgcc accatggcca  5820
ccggctctcg cacaagcctg ctgctggctt tcggactgct gtgcctgcct tggctccagg  5880
agggctccgc cgctagcatc gataccgtcg ctatgtgctg gaggcttgct gaaggctgta  5940
tgctgtttct tcatcgtgcc ttcttcgcgt tttggcctct gactgacgcg aagaaggcga  6000
tgaagaaaca ggacacaagg cctgttacta gcactcacat ggaacaaatg gcctctagcc  6060
tggaggcttg ctgaaggctg tatgctgtct tcatcgccat ttcttcgcgt tttggcctct  6120
gactgacgcg aagaaggcga tgaagacagg acacaaggcc tgttactagc actcacatgg  6180
aacaaatggc ctctagcctg gaggcttgct gaaggctgta tgctgaaact ggctgtaata  6240
tcgcgcgttt tggcctctga ctgacgcgcg ataacagcca gtttcaggac acaaggcctg  6300
ttactagcac tcacatggaa caaatggcct c                                6331
```

COMPOSITION FOR REGULATING PRODUCTION OF INTERFERING RIBONUCLEIC ACID

CROSS-REFERENCE TO RELATED APPLICATION

The present application is a continuation of U.S. patent application Ser. No. 18/913,381 filed Oct. 11, 2024, entitled "COMPOSITION FOR REGULATING PRODUCTION OF INTERFERING RIBONUCLEIC ACID" currently pending, the entirety of which is incorporated herein by reference.

SEQUENCE LISTING

This application contains a Sequence Listing electronically submitted via Patent Center to the United States Patent and Trademark Office as an XML Document file entitled "A8149859US-SequenceListing2.xml" created on 2024 Dec. 17 and having a size of 16,096 bytes. The information contained in the Sequence Listing is incorporated by reference herein.

TECHNICAL FIELD

The present disclosure generally relates to compositions for regulating production of micro-interfering ribonucleic acid (miRNA). In particular, the present disclosure relates to compositions for regulating gene expression and as a result, the production of miRNA that will suppress cytokine over-expression or mis-expression.

BACKGROUND

Bioactive molecules, including cytokines, are necessary for the homeostatic control of biological systems.

When bioactive molecules are over-expressed or mis-expressed, homeostasis is lost, and disease is often the result.

As such, it may be desirable to establish therapies, treatments and/or interventions that address the loss of homeostasis and mis-regulation of bioactive molecules in order to prevent or treat a resulting disease.

SUMMARY

Some embodiments of the present disclosure relate to one or more compositions that upregulate the production of one or more sequences of micro-interfering ribonucleic acid (miRNA). The sequences of miRNA may be complementary to a sequence of target messenger RNA (mRNA) that encodes for the translation of a target biomolecule, and the miRNA can cause the bioavailability of the target mRNA to decrease because it is degraded and/or inactivated by the miRNA, thereby causing a decrease in bioavailability of the target biomolecule within a subject that is administered the one or more compositions. In some embodiments of the present disclosure, the target biomolecule is a cytokine. In some embodiments of the present disclosure, the target biomolecule is a cytokine such as IL-23.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates the introduction of the one or more insert sequences into one or more of a subject's cells, where it is expressed and/or replicated. Expression of the one or more insert sequences by one or more of the subject's cells results in an increased production of the miRNA and, therefore, decreased translation or production of the target biomolecule by one or more of the subject's cells. In some embodiments of the present disclosure, the plasmid is a circular vector with a backbone sequence that comprises a start region, for example at the 3' end of the sequence, and an end region, for example at the 5' end of the sequence. The one or more insert sequences are inserted into the backbone sequence so as to connect the start region to the end region. For example, the one or more insert sequences may be inserted to connected at both the 3' end of the backbone sequence and the 5' end of the backbone sequence in order to connect the two ends of the backbone sequence so as to form the circular vector.

Some embodiments of the present disclosure relate to compositions that upregulate the production of miRNA that degrades or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 combined with SEQ ID NO. 2. The RP comprises a nucleotide sequence encoding for one or more nucleotide sequences encoding for an miRNA sequence that targets the mRNA of IL-23.

Some embodiments of the present disclosure relate to a method of making a composition/target cell complex. The method comprising a step of administering an RP comprising SEQ ID NO. 1 combined with SEQ ID NO. 2 to a target cell for forming the composition/target cell complex, wherein the composition/target cell complex causes the target cell to increase the production of one or more sequences of miRNA that decreases production of a target biomolecule.

Some embodiments of the present disclosure relate to at least one approach for inducing endogenous production of one or more sequences of miRNA that target and silence the mRNA of a target biomolecule, for example IL-23. A first approach utilizes gene vectors containing nucleotide sequences for increasing the endogenous production of one or more sequences of miRNA, which are complete or partial sequences and/or combinations thereof, that target and silence the mRNA of IL-23, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "ameliorate" refers to improve and/or to make better and/or to make more satisfactory.

As used therein, the term "biomolecule" refers to a cytokine that is found within a subject. A biomolecule may be endogenous or exogenous to a subject.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector (AAV).

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target biomolecule protein is produced.

In some embodiments of the present disclosure, the target biomolecule is IL-23.

In some embodiments of the present disclosure, the insert comprises one or more nucleotide sequences that each encode for one or more miRNA sequences that may be complementary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the production and/or functionality of one or more of the subject's biomolecules may change.

In some embodiments of the present disclosure, the production and/or functionality of one or more of the subject's intermediary molecules may change in response to the subject receiving a therapeutic amount of the composition, thereby changing production of one or more DNA sequences, one or more RNA sequences, and/or one or more proteins that regulate the levels and/or functionality of the one or more intermediary molecules. The one or more intermediary molecules may regulate the subject's levels and/or functionality of the one or more biomolecules.

In some embodiments of the present disclosure, administering a therapeutic amount of the composition to a subject upregulates the production, functionality or both of one or more sequences of miRNA that each target the mRNA of one or more target biomolecules. In some embodiments of the present disclosure, there are one, two, three, four, five, or six miRNA sequences that each are complementary to and degrade, or cause degradation of, one biomolecule, such as IL-23. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause an increased production of one or more nucleotide sequences that cause an increased production of one or more miRNA sequences that are each complementary to and degrade, or cause degradation of, or inactivate, or cause inactivation of, one biomolecule, such as IL-23. Increased endogenous expression of the one or more miRNA sequences results in a decreased bioavailability of the desired biomolecule, which may also be referred to as a target biomolecule.

In some embodiments of the present disclosure, the delivery vehicle for the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle for the RP used for gene therapy may be a protein coat.

In some embodiments of the present disclosure, the delivery vehicle for the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ $TCID_{50}$/kg (50% tissue culture infective dose per kilogram of the patient's body mass). In some embodiments of the present disclosure, the therapeutically effective amount of the composition that is administered to the patient is about $1\times10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1\times10^{16}$ TCP/kg.

Some embodiments of the present disclosure relate to an adenovirus associated virus (AAV) genome consisting of an RP that when operable inside a target cell will cause the target cell to produce a miRNA sequence that downregulates production of a biomolecule, with an example being IL-23. The RP is comprised of AAV2 inverted terminal repeats (ITRs), a composite CASI promoter, a human growth hormone (HGH) signal peptide followed by a miRNA expression cassette containing up to six different miRNAs targeting IL-23, followed by a Woodchuck Hepatitis Virus post-transcriptional regulatory element (WPRE) and an SV40 polyA signal.

```
SEQ ID NO. 1 (backbone sequence No. 1):
5' TCTAGAATAATCAACCTCTGGATTACAAAATTTGTGAAAGATTGACTGGTATTCTTAAC

TATGTTGCTCCTTTTACGCTATGTGGATACGCTGCTTTAATGCCTTTGTATCATGCTATT

GCTTCCCGTATGGCTTTCATTTTCTCCTCCTTGTATAAATCCTGGTTGCTGTCTCTTTAT

GAGGAGTTGTGGCCCGTTGTCAGGCAACGTGGCGTGGTGTGCACTGTGTTTGCTGAC

GCAACCCCCACTGGTTGGGGCATTGCCACCACCTGTCAGCTCCTTTCCGGGACTTTC

GCTTTCCCCCTCCCTATTGCCACGGCGGAACTCATCGCCGCCTGCCTTGCCCGCTGCT

GGACAGGGGCTCGGCTGTTGGGCACTGACAATTCCGTGGTGTTGTCGGGGAAATCAT

CGTCCTTTCCTTGGCTGCTCGCCTGTGTTGCCACCTGGATTCTGCGCGGGACGTCCTT

CTGCTACGTCCCTTCGGCCCTCAATCCAGCGGACCTTCCTTCCCGCGGCCTGCTGCCG

GCTCTGCGGCCTCTTCCGCGTCTTCGCCTTCGCCCTCAGACGAGTCGGATCTCCCTTT

GGGCCGCCTCCCCGCCTAAGCTTATCGATACCGTCGAGATCTAACTTGTTTATTGCAGC

TTATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGATCT
```

-continued

CGACCTCGACTAGAGCATGGCTACGTAGATAAGTAGCATGGCGGGTTAATCATTAACT

ACAAGGAACCCCTAGTGATGGAGTTGGCCACTCCCTCTCTGCGCGCTCGCTCGCTCA

CTGAGGCCGGGCGACCAAAGGTCGCCCGACGCCCGGGCTTTGCCCGGGCGGCCTCA

GTGAGCGAGCGAGCGCGCAGCTGGCGTAATAGCGAAGAGGCCCGCACCGATCGCCC

TTCCCAACAGTTGCGCAGCCTGAATGGCGAATGGCGATTCCGTTGCAATGGCTGGCG

GTAATATTGTTCTGGATATTACCAGCAAGGCCGATAGTTTGAGTTCTTCTACTCAGGCA

AGTGATGTTATTACTAATCAAAGAAGTATTGCGACAACGGTTAATTTGCGTGATGGAC

AGACTCTTTTACTCGGTGGCCTCACTGATTATAAAAACACTTCTCAGGATTCTGGCGT

ACCGTTCCTGTCTAAAATCCCTTTAATCGGCCTCCTGTTTAGCTCCCGCTCTGATTCTA

ACGAGGAAAGCACGTTATACGTGCTCGTCAAAGCAACCATAGTACGCGCCCTGTAGC

GGCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTTA

CGGCACCTCGACCCCAAAAAACTTGATTAGGGTGATGGTTCACGTAGTGGGCCATCG

CCCTGATAGACGGTTTTTCGCCCTTTGACGTTGGAGTCCACGTTCTTTAATAGTGGAC

TCTTGTTCCAAACTGGAACAACACTCAACCCTATCTCGGTCTATTCTTTTGATTTATAA

GGGATTTTGCCGATTTCGGCCTATTGGTTAAAAAATGAGCTGATTTAACAAAAATTTA

ACGCGAATTTTAACAAAATATTAACGTTTACAATTTAAATATTTGCTTATACAATCTTCC

TGTTTTTGGGGCTTTTCTGATTATCAACCGGGGTACATATGATTGACATGCTAGTTTTAC

GATTACCGTTCATCGATTCTCTTGTTTGCTCCAGACTCTCAGGCAATGACCTGATAGCC

TTTGTAGAGACCTCTCAAAAATAGCTACCCTCTCCGGCATGAATTTATCAGCTAGAAC

GGTTGAATATCATATTGATGGTGATTTGACTGTCTCCGGCCTTTCTCACCCGTTTGAAT

CTTTACCTACACATTACTCAGGCATTGCATTTAAAATATATGAGGGTTCTAAAAATTTTT

ATCCTTGCGTTGAAATAAAGGCTTCTCCCGCAAAAGTATTACAGGGTCATAATGTTTTT

GGTACAACCGATTTAGCTTTATGCTCTGAGGCTTTATTGCTTAATTTTGCTAATTCTTTG

CCTTGCCTGTATGATTTATTGGATGTTGGAATTCCTGATGCGGTATTTTCTCCTTACGCA

TCTGTGCGGTATTTCACACCGCATATGGTGCACTCTCAGTACAATCTGCTCTGATGCCG

CATAGTTAAGCCAGCCCCGACACCCGCCAACACCCGCTGACGCGCCCTGACGGGCTT

GTCTGCTCCCGGCATCCGCTTACAGACAAGCTGTGACCGTCTCCGGGAGCTGCATGT

GTCAGAGGTTTTCACCGTCATCACCGAAACGCGCGAGACGAAAGGGCCTCGTGATAC

GCCTATTTTTATAGGTTAATGTCATGATAATAATGGTTTCTTAGACGTCAGGTGGCACTT

TTCGGGGAAATGTGCGCGGAACCCCTATTTGTTTATTTTTCTAAATACATTCAAATATG

TATCCGCTCATGAGACAATAACCCTGATAAATGCTTCAATAATATTGAAAAAGGAAGA

GTATGAGTATTCAACATTTCCGTGTCGCCCTTATTCCCTTTTTTGCGGCATTTTGCCTTC

CTGTTTTTGCTCACCCAGAAACGCTGGTGAAAGTAAAAGATGCTGAAGATCAGTTGG

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCGC

GGTATTATCCCGTATTGACGCCGGGCAAGAGCAACTCGGTCGCCGCATACACTATTCT

CAGAATGACTTGGTTGAGTACTCACCAGTCACAGAAAAGCATCTTACGGATGGCATG

ACAGTAAGAGAATTATGCAGTGCTGCCATAACCATGAGTGATAACACTGCGGCCAACT

-continued

TACTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATACCAA

ACGACGAGCGTGACACCACGATGCCTGTAGCAATGGCAACAACGTTGCGCAAACTAT

TAACTGGCGAACTACTTACTCTAGCTTCCCGGCAACAATTAATAGACTGGATGGAGGC

GGATAAAGTTGCAGGACCACTTCTGCGCTCGGCCCTTCCGGCTGGCTGGTTTATTGCT

GATAAATCTGGAGCCGGTGAGCGTGGGTCTCGCGGTATCATTGCAGCACTGGGGCCA

GATGGTAAGCCCTCCCGTATCGTAGTTATCTACACGACGGGGAGTCAGGCAACTATGG

ATGAACGAAATAGACAGATCGCTGAGATAGGTGCCTCACTGATTAAGCATTGGTAACT

GTCAGACCAAGTTTACTCATATATACTTTAGATTGATTTAAAACTTCATTTTTAATTTAA

AAGGATCTAGGTGAAGATCCTTTTTGATAATCTCATGACCAAAATCCCTTAACGTGAG

TTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGT

GGTTTGTTTGCCGGATCAAGAGCTACCAACTCTTTTTCCGAAGGTAACTGGCTTCAGC

AGAGCGCAGATACCAAATACTGTCCTTCTAGTGTAGCCGTAGTTAGGCCACCACTTCA

AGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCG

AACGACCTACACCGAACTGAGATACCTACAGCGTGAGCTATGAGAAAGCGCCACGCT

TCCCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGGCGGAGCC

TATGGAAAAACGCCAGCAACGCGGCCTTTTTACGGTTCCTGGCCTTTTGCTGGCCTTT

TGCTCACATGTTCTTTCCTGCGTTATCCCCTGATTCTGTGGATAACCGTATTACCGCCTT

TGAGTGAGCTGATACCGCTCGCCGCAGCCGAACGACCGAGCGCAGCGAGTCAGTGA

GCGAGGAAGCGGAAGAGCGCCCAATACGCAAACCGCCTCTCCCCGCGCGTTGGCCG

ATTCATTAATGCAGCAGCTGCGCGCTCGCTCGCTCACTGAGGCCGCCCGGGCAAAGC

CCGGGCGTCGGGCGACCTTTGGTCGCCCGGCCTCAGTGAGCGAGCGAGCGCGCAGA

GAGGGAGTGGCCAACTCCATCACTAGGGGTTCCTTGTAGTTAATGATTAACCCGCCAT

GCTACTTATCTACGTAGCCATGCTCTAGGACATTGATTATTGACTAGTGGAGTTCCGCG

TTACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACGTC

AATGGGTGGAGTATTTACGGTAAACTGCCCACTTGGCAGTACATCAAGTGTATCATAT

GCCAAGTACGCCCCCTATTGACGTCAATGACGGTAAATGGCCCGCCTGGCATTATGCC

CAGTACATGACCTTATGGGACTTTCCTACTTGGCAGTACATCTACGTATTAGTCATCGC

TATTACCATGGTCGAGGTGAGCCCCACGTTCTGCTTCACTCTCCCCATCTCCCCCCCCT

CCCCACCCCCAATTTTGTATTTATTTATTTTTTAATTATTTTGTGCAGCGATGGGGGCGG

GGGGGGGGGGGGCGCGCGCCAGGCGGGGCGGGGCGGGGCGAGGGGGGGGGGGG

GGCGAGGCGGAGAGGTGCGGCGGCAGCCAATCAGAGCGGCGCGCTCCGAAAGTTTC

CTTTTATGGCGAGGCGGCGGCGGCGGCGGCCCTATAAAAAGCGAAGCGCGCGGCGG

GCGGGAGTCGCTGCGCGCTGCCTTCGCCCCGTGCCCCGCTCCGCCGCCGCCTCGCGC

CGCCCGCCCCGGCTCTGACTGACCGCGTTACTAAAACAGGTAAGTCCGGCCTCCGCG

-continued

CCGGGTTTTGGCGCCTCCCGCGGGCGCCCCCCTCCTCACGGCGAGCGCTGCCACGTC

AGACGAAGGGCGCAGCGAGCGTCCTGATCCTTCCGCCCGGACGCTCAGGACAGCGG

CCCGCTGCTCATAAGACTCGGCCTTAGAACCCCAGTATCAGCAGAAGGACATTTTAGG

ACGGGACTTGGGTGACTCTAGGGCACTGGTTTTCTTTCCAGAGAGCGGAACAGGCGA

GGAAAAGTAGTCCCTTCTCGGCGATTCTGCGGAGGGATCTCCGTGGGGCGGTGAACG

CCGATGATGCCTCTACTAACCATGTTCATGTTTTCTTTTTTTTTCTACAGGTCCTGGGTG

ACGAACAGGGTACC 3'

SEQ ID NO. 2 (miRNA expression cassette IL-23):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGA

GGCTTGCTGAAGGCTGTATGCTGTTTCTTCATCGTGCCTTCTTCGCGTTTTGGCCTCTG

ACTGACGCGAAGAAGGCGATGAAGAAACAGGACACAAGGCCTGTTACTAGCACTCA

CATGGAACAAATGGCCTCTAGCCTGGAGGCTTGCTGAAGGCTGTATGCTGTCTTCATC

GCCATTTCTTCGCGTTTTGGCCTCTGACTGACGCGAAGAAGGCGATGAAGACAGGAC

ACAAGGCCTGTTACTAGCACTCACATGGAACAAATGGCCTCTAGCCTGGAGGCTTGC

TGAAGGCTGTATGCTGAAACTGGCTGTAATATCGCGCGTTTTGGCCTCTGACTGACGC

GCGATAACAGCCAGTTTCAGGACACAAGGCCTGTTACTAGCACTCACATGGAACAAA

TGGCCTC 3'

As will be appreciated by those skilled in the art, when SEQ ID NO. 2 for the miRNA expression cassettes is inserted into the backbone sequence (SEQ ID NO. 1), the resultant vector is circular, with one or more miRNA expression cassettes inserted between the 5' and 3' ends of SEQ ID NO. 1. Accordingly, the following sequences represent further sequence listings that form part of this disclosure and that comprise SEQ ID NO. 1 with SEQ ID NO. 2 inserted.

SEQ ID NO. 3 = SEQ ID NO. 1 combined with SEQ ID NO. 2:
5' TCTAGAATAATCAACCTCTGGATTACAAAATTTGTGAAAGATTGACTGGTATTCTTAAC

TATGTTGCTCCTTTTACGCTATGTGGATACGCTGCTTTAATGCCTTTGTATCATGCTATT

GCTTCCCGTATGGCTTTCATTTTCTCCTCCTTGTATAAATCCTGGTTGCTGTCTCTTTAT

GAGGAGTTGTGGCCCGTTGTCAGGCAACGTGGCGTGGTGTGCACTGTGTTTGCTGAC

GCAACCCCCACTGGTTGGGGCATTGCCACCACCTGTCAGCTCCTTTCCGGGACTTTC

GCTTTCCCCCTCCCTATTGCCACGGCGGAACTCATCGCCGCCTGCCTTGCCCGCTGCT

GGACAGGGGCTCGGCTGTTGGGCACTGACAATTCCGTGGTGTTGTCGGGGAAATCAT

CGTCCTTTCCTTGGCTGCTCGCCTGTGTTGCCACCTGGATTCTGCGCGGGACGTCCTT

CTGCTACGTCCCTTCGGCCCTCAATCCAGCGGACCTTCCTTCCCGCGGCCTGCTGCCG

GCTCTGCGGCCTCTTCCGCGTCTTCGCCTTCGCCCTCAGACGAGTCGGATCTCCCTTT

GGGCCGCCTCCCCGCCTAAGCTTATCGATACCGTCGAGATCTAACTTGTTTATTGCAGC

TTATAATGGTTACAAATAAAGCAATAGCATCACAAATTTCACAAATAAAGCATTTTTTT

CACTGCATTCTAGTTGTGGTTTGTCCAAACTCATCAATGTATCTTATCATGTCTGGATCT

CGACCTCGACTAGAGCATGGCTACGTAGATAAGTAGCATGGCGGGTTAATCATTAACT

ACAAGGAACCCCTAGTGATGGAGTTGGCCACTCCCTCTCTGCGCGCTCGCTCGCTCA

CTGAGGCCGGGCGACCAAAGGTCGCCCGACGCCCGGGCTTTGCCCGGGCGGCCTCA

GTGAGCGAGCGAGCGCGCAGCTGGCGTAATAGCGAAGAGGCCCGCACCGATCGCCC

TTCCCAACAGTTGCGCAGCCTGAATGGCGAATGGCGATTCCGTTGCAATGGCTGGCG

-continued

GTAATATTGTTCTGGATATTACCAGCAAGGCCGATAGTTTGAGTTCTTCTACTCAGGCA

AGTGATGTTATTACTAATCAAAGAAGTATTGCGACAACGGTTAATTTGCGTGATGGAC

AGACTCTTTTACTCGGTGGCCTCACTGATTATAAAAACACTTCTCAGGATTCTGGCGT

ACCGTTCCTGTCTAAAATCCCTTTAATCGGCCTCCTGTTTAGCTCCCGCTCTGATTCTA

ACGAGGAAAGCACGTTATACGTGCTCGTCAAAGCAACCATAGTACGCGCCCTGTAGC

GGCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTTA

CGGCACCTCGACCCCAAAAAACTTGATTAGGGTGATGGTTCACGTAGTGGGCCATCG

CCCTGATAGACGGTTTTTCGCCCTTTGACGTTGGAGTCCACGTTCTTTAATAGTGGAC

TCTTGTTCCAAACTGGAACAACACTCAACCCTATCTCGGTCTATTCTTTTGATTTATAA

GGGATTTTGCCGATTTCGGCCTATTGGTTAAAAAATGAGCTGATTTAACAAAAATTTA

ACGCGAATTTTAACAAAATATTAACGTTTACAATTTAAATATTTGCTTATACAATCTTCC

TGTTTTTGGGGCTTTTCTGATTATCAACCGGGGTACATATGATTGACATGCTAGTTTTAC

GATTACCGTTCATCGATTCTCTTGTTTGCTCCAGACTCTCAGGCAATGACCTGATAGCC

TTTGTAGAGACCTCTCAAAAATAGCTACCCTCTCCGGCATGAATTTATCAGCTAGAAC

GGTTGAATATCATATTGATGGTGATTTGACTGTCTCCGGCCTTTCTCACCCGTTTGAAT

CTTTACCTACACATTACTCAGGCATTGCATTTAAAATATATGAGGGTTCTAAAAATTTTT

ATCCTTGCGTTGAAATAAAGGCTTCTCCCGCAAAAGTATTACAGGGTCATAATGTTTTT

GGTACAACCGATTTAGCTTTATGCTCTGAGGCTTTATTGCTTAATTTTGCTAATTCTTTG

CCTTGCCTGTATGATTTATTGGATGTTGGAATTCCTGATGCGGTATTTTCTCCTTACGCA

TCTGTGCGGTATTTCACACCGCATATGGTGCACTCTCAGTACAATCTGCTCTGATGCCG

CATAGTTAAGCCAGCCCCGACACCCGCCAACACCCGCTGACGCGCCCTGACGGGCTT

GTCTGCTCCCGGCATCCGCTTACAGACAAGCTGTGACCGTCTCCGGGAGCTGCATGT

GTCAGAGGTTTTCACCGTCATCACCGAAACGCGCGAGACGAAAGGGCCTCGTGATAC

GCCTATTTTTATAGGTTAATGTCATGATAATAATGGTTTCTTAGACGTCAGGTGGCACTT

TTCGGGGAAATGTGCGCGGAACCCCTATTTGTTTATTTTTCTAAATACATTCAAATATG

TATCCGCTCATGAGACAATAACCCTGATAAATGCTTCAATAATATTGAAAAAGGAAGA

GTATGAGTATTCAACATTTCCGTGTCGCCCTTATTCCCTTTTTTGCGGCATTTTGCCTTC

CTGTTTTTGCTCACCCAGAAACGCTGGTGAAAGTAAAAGATGCTGAAGATCAGTTGG

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCGC

GGTATTATCCCGTATTGACGCCGGGCAAGAGCAACTCGGTCGCCGCATACACTATTCT

CAGAATGACTTGGTTGAGTACTCACCAGTCACAGAAAAGCATCTTACGGATGGCATG

ACAGTAAGAGAATTATGCAGTGCTGCCATAACCATGAGTGATAACACTGCGGCCAACT

TACTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATACCAA

ACGACGAGCGTGACACCACGATGCCTGTAGCAATGGCAACAACGTTGCGCAAACTAT

TAACTGGCGAACTACTTACTCTAGCTTCCCGGCAACAATTAATAGACTGGATGGAGGC

GGATAAAGTTGCAGGACCACTTCTGCGCTCGGCCCTTCCGGCTGGCTGGTTTATTGCT

GATAAATCTGGAGCCGGTGAGCGTGGGTCTCGCGGTATCATTGCAGCACTGGGGCCA

-continued

GATGGTAAGCCCTCCCGTATCGTAGTTATCTACACGACGGGGAGTCAGGCAACTATGG

ATGAACGAAATAGACAGATCGCTGAGATAGGTGCCTCACTGATTAAGCATTGGTAACT

GTCAGACCAAGTTTACTCATATATACTTTAGATTGATTTAAAACTTCATTTTTAATTTAA

AAGGATCTAGGTGAAGATCCTTTTTGATAATCTCATGACCAAAATCCCTTAACGTGAG

TTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGT

GGTTTGTTTGCCGGATCAAGAGCTACCAACTCTTTTTCCGAAGGTAACTGGCTTCAGC

AGAGCGCAGATACCAAATACTGTCCTTCTAGTGTAGCCGTAGTTAGGCCACCACTTCA

AGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCG

AACGACCTACACCGAACTGAGATACCTACAGCGTGAGCTATGAGAAAGCGCCACGCT

TCCCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGGCGGAGCC

TATGGAAAAACGCCAGCAACGCGGCCTTTTTACGGTTCCTGGCCTTTTGCTGGCCTTT

TGCTCACATGTTCTTTCCTGCGTTATCCCCTGATTCTGTGGATAACCGTATTACCGCCTT

TGAGTGAGCTGATACCGCTCGCCGCAGCCGAACGACCGAGCGCAGCGAGTCAGTGA

GCGAGGAAGCGGAAGAGCGCCCAATACGCAAACCGCCTCTCCCCGCGCGTTGGCCG

ATTCATTAATGCAGCAGCTGCGCGCTCGCTCGCTCACTGAGGCCGCCCGGGCAAAGC

CCGGGCGTCGGGCGACCTTTGGTCGCCCGGCCTCAGTGAGCGAGCGAGCGCGCAGA

GAGGGAGTGGCCAACTCCATCACTAGGGGTTCCTTGTAGTTAATGATTAACCCGCCAT

GCTACTTATCTACGTAGCCATGCTCTAGGACATTGATTATTGACTAGTGGAGTTCCGCG

TTACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACGTC

AATGGGTGGAGTATTTACGGTAAACTGCCCACTTGGCAGTACATCAAGTGTATCATAT

GCCAAGTACGCCCCCTATTGACGTCAATGACGGTAAATGGCCCGCCTGGCATTATGCC

CAGTACATGACCTTATGGGACTTTCCTACTTGGCAGTACATCTACGTATTAGTCATCGC

TATTACCATGGTCGAGGTGAGCCCCACGTTCTGCTTCACTCTCCCCATCTCCCCCCCCT

CCCCACCCCCAATTTTGTATTTATTTATTTTTTAATTATTTTGTGCAGCGATGGGGGCGG

GGGGGGGGGGGGGCGCGCGCCAGGCGGGGGGGGGGGGGCGAGGGGGGGGGGGG

GGCGAGGCGGAGAGGTGCGGCGGCAGCCAATCAGAGCGGCGCGCTCCGAAAGTTTC

CTTTTATGGCGAGGCGGCGGCGGCGGCGGCCCTATAAAAAGCGAAGCGCGCGGCGG

GCGGGAGTCGCTGCGCGCTGCCTTCGCCCCGTGCCCCGCTCCGCCGCCGCCTCGCGC

CGCCCGCCCCGGCTCTGACTGACCGCGTTACTAAAACAGGTAAGTCCGGCCTCCGCG

CCGGGTTTTGGCGCCTCCCGCGGGCGCCCCCCTCCTCACGGCGAGCGCTGCCACGTC

AGACGAAGGGCGCAGCGAGCGTCCTGATCCTTCCGCCCGGACGCTCAGGACAGCGG

CCCGCTGCTCATAAGACTCGGCCTTAGAACCCCAGTATCAGCAGAAGGACATTTTAGG

ACGGGACTTGGGTGACTCTAGGGCACTGGTTTTCTTTCCAGAGAGCGGAACAGGCGA

GGAAAAGTAGTCCCTTCTCGGCGATTCTGCGGAGGGATCTCCGTGGGGCGGTGAACG

-continued

```
CCGATGATGCCTCTACTAACCATGTTCATGTTTTCTTTTTTTTTCTACAGGTCCTGGGTG

ACGAACAGGGTACCGCCACCATGGCCACCGGCTCTCGCACAAGCCTGCTGCTGGCTT

TCGGACTGCTGTGCCTGCCTTGGCTCCAGGAGGGCTCCGCCGCTAGCATCGATACCGT

CGCTATGTGCTGGAGGCTTGCTGAAGGCTGTATGCTGTTTCTTCATCGTGCCTTCTTCG

CGTTTTGGCCTCTGACTGACGCGAAGAAGGCGATGAAGAAACAGGACACAAGGCCT

GTTACTAGCACTCACATGGAACAAATGGCCTCTAGCCTGGAGGCTTGCTGAAGGCTG

TATGCTGTCTTCATCGCCATTTCTTCGCGTTTTGGCCTCTGACTGACGCGAAGAAGGC

GATGAAGACAGGACACAAGGCCTGTTACTAGCACTCACATGGAACAAATGGCCTCTA

GCCTGGAGGCTTGCTGAAGGCTGTATGCTGAAACTGGCTGTAATATCGCGCGTTTTGG

CCTCTGACTGACGCGCGATAACAGCCAGTTTCAGGACACAAGGCCTGTTACTAGCAC

TCACATGGAACAAATGGCCTC 3'
```

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% (i.e. at least 95%) nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes were integrated with the pAVA-00200 backbone via homologous recombination. The resulting RP contained the following: 5' ITR, CASI promoter, miRNA expression cassette, WPRE, SV40 polyA and ITR 3'.

What is claimed is:

1. A composition that comprises a recombinant plasmid (RP) comprising a sequence of nucleotides that is SEQ ID NO. 3.

2. The composition of claim 1, wherein the RP is encapsulated in a protein coat, a lipid vesicle, or any combination thereof.

* * * * *